United States Patent [19]
Hoftman et al.

[11] Patent Number: 5,820,086
[45] Date of Patent: Oct. 13, 1998

[54] I.V. POLE AND IRRIGATION TOWER AND SUPPORT SYSTEM

[76] Inventors: Mike M. Hoftman, 21026 Osborne St., Canoga Park, Calif. 91304; Patricia C. Andersen, 827 Cypress St., Thousand Oaks, Calif. 91360

[21] Appl. No.: 316,564

[22] Filed: Sep. 30, 1994

Related U.S. Application Data

[63] Continuation of Ser. No. 843,392, Feb. 28, 1992, abandoned.

[51] Int. Cl.⁶ ........................................ A47G 29/00
[52] U.S. Cl. .................. 248/125.2; 248/158; 248/295.11
[58] Field of Search ................................ 248/125.1, 121, 248/124.1, 123.11, 320, 129, 297.2, 414, 295.11, 297.11, 328, 332, 158, 125.2

[56] References Cited

U.S. PATENT DOCUMENTS

| | | | |
|---|---|---|---|
| 730,358 | 6/1903 | Fladby | 248/295.1 |
| 1,182,706 | 5/1916 | Priest | 248/297.3 |
| 1,195,448 | 8/1916 | Dolechek | 248/295.1 |
| 1,347,846 | 7/1920 | Gelb | 248/123.1 X |
| 1,575,177 | 3/1926 | Moran | 248/328 |
| 2,569,622 | 10/1951 | Trainor | 248/297.2 X |
| 2,677,519 | 5/1954 | Hobson | 248/125 |
| 3,191,903 | 6/1965 | Wieland | 248/328 |
| 4,332,378 | 6/1982 | Peyor | 248/125 X |
| 5,110,076 | 5/1992 | Synder et al. | 248/125 |
| 5,188,323 | 2/1993 | David | 248/158 |

FOREIGN PATENT DOCUMENTS

| | | | |
|---|---|---|---|
| 132363 | 3/1933 | Germany | 248/124 |

OTHER PUBLICATIONS

Promotional advertisement describing an I.V. support stand referred to by the trademark "Stat–Stand" model 1050 by I.V. League Medical.

Promotional advertisement describing an I.V. and irrigation tower produced by Allen Medical Systems.

*Primary Examiner*—Ramon O. Ramirez

[57] ABSTRACT

An I.V. pole irrigation tower comprises a pole and a base. The base has a hub and legs spaced apart about the hub and extending outwardly at an angle away from the hub. Each leg further includes dual casters secured thereto for moving the base. The pole has a lower end secured to the hub of the base and a plurality of sections fastened together in interlocking relationship. Each section includes a channel for housing a pulley system, the pulley system has a support bar attached thereto for supporting at least one fluid bag. Each section also includes a channel for housing an associated pulley system, the pulley system having a support bar attached thereto for supporting at least one fluid bag. Each section also includes a handle assembly coupled to the pulley system for adjusting the height of the support hanger along the length of the section. A spring-biased lever is coupled to the handle assembly for locking the handle assembly and support bar at a predetermined location along the length of the pole.

16 Claims, 8 Drawing Sheets

I.V. POLE AND IRRIGATION TOWER AND SUPPORT SYSTEM

This is a continuation of application Ser. No. 07/843,392 filed on Feb. 28, 1992 now abandoned.

BACKGROUND OF THE INVENTION

1. Field of the Invention

The present invention relates in general to an (intravenous) I.V. pole and irrigation tower and support system used to support fluid bags for use in the treatment of patients, and during surgery for irrigation.

2. Description of the Related Art

I.V. poles, irrigation towers and support systems are commonly used in hospitals, homes and ambulances to support fluid bags containing intravenous or I.V. fluids and/or irrigation fluids for use in the treatment of patients and during surgery. It is often desirable to have such irrigation towers support a large number of fluid bags. It is also desirable that these fluid bags contain a large amount of fluid so that these bags do not have to be replaced as often. They are also more economical per liter. However, both the use of a large number of fluid bags and the use of heavy bags contribute to additional weight or unbalanced weight which the irrigation tower must stably support.

Due to the slim profile of these irrigation towers and the large number of heavy bags that typically hang therefrom, it is important to provide these towers with a stable base for adequate stability and to prevent these towers from toppling over. Many of the current irrigation towers lack such a stable base, which precludes the use therewith of either a larger number of fluid bags or fluid bags containing large volumes of fluid. Many of the current irrigation towers use a base that has four legs, which do not provide proper stability. This is true especially if heavy fluid bags are supported from only one side of the tower, so that the tower is likely to topple to that side. Furthermore, the lack of a stable base poses a safety concern because such irrigation towers may tip over and cause damage to the fluid bags or to the surrounding environment.

Another problem encountered by current irrigation towers relates to the adjustment of the support height of the fluid bags. Most I.V. poles and irrigation towers are provided with a metal rod from which fluid bags are supported. To adjust the height of a given fluid bag, an operator must push a handle immediately connected to the metal rod upwards or downwards or other styles require one to loosen the center rod and slide all bags with the inner rod upward with two hands and then when one reaches the proper height, secure the center rod by turning and locking the pole. Given the heavy weight of some of these fluid bags, such height adjustment requires a great deal of force to push the handle or rod up and down. Sometimes, excessive force used to adjust the height of the fluid bags may cause damage to the fluid bags or cause the irrigation tower to topple.

SUMMARY OF THE DISCLOSURE

In order to accomplish the objects of the present invention, an irrigation tower according to embodiments of the present invention comprises a base having a hub and at least four and preferably five legs spaced apart about the hub. Each leg has a first end secured to the hub and a second end extending outwardly at an angle away from the hub so that the second end of each leg assumes a position which is either the same level (horizontal) or vertically higher than the position of the first end, with each leg further including dual casters secured to the second end for ease of moving the base.

This irrigation tower further comprises a pole comprising a lower end secured to the hub of the base and a support base trunk with a plurality of channels as one piece or fastened together in interlocking relationship. Each section includes a channel for housing a pulley system, the pulley system having a support bar attached thereto for supporting at least one fluid bag. Each section also includes a handle assembly coupled to the pulley system for adjusting the height of the support bar along the length of the section, the handle assembly including a spring-biased lever for locking the handle assembly and support bar at any predetermined position along the length of the section. The pulley system can provide a mechanical advantage as well.

The irrigation tower according to embodiments of the present invention provides a simple yet stable base which effectively prevents the tower from toppling over. The provision of at least four legs for the base together with their level or angled orientation provide additional stability to the tower so that fluid bags containing a larger volume of fluid can be supported therefrom without any fear of toppling the irrigation tower.

This irrigation tower also has a pulley system which reduces the amount of force that an operator needs to apply in order to move the handle assembly upwards or downwards, thereby making it easier for an operator to adjust the height of the support hanger bars and the fluid bags thereon without having to exert excessive force or pressure. The handle assembly for use in adjusting the height of the support bars is further equipped with a simple and easy-to-use locking mechanism. In addition the pulley mechanism enables the user to use the more natural push down technique to lift the bag up, rather than the normal pulling up action with all I.V. poles. Further, the configuration of each support hanger provides a stable support for two fluid bags. These all provide for an irrigation tower which is safer, more efficient and more economical.

BRIEF DESCRIPTION OF THE DRAWINGS

Further objects, advantages and features of the invention will become apparent from the detailed description of the preferred embodiments when read in conjunction with the accompanying drawings, in which.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating general principles of embodiments of the invention. The scope of the invention is best defined by the appended claims.

Figure 1:
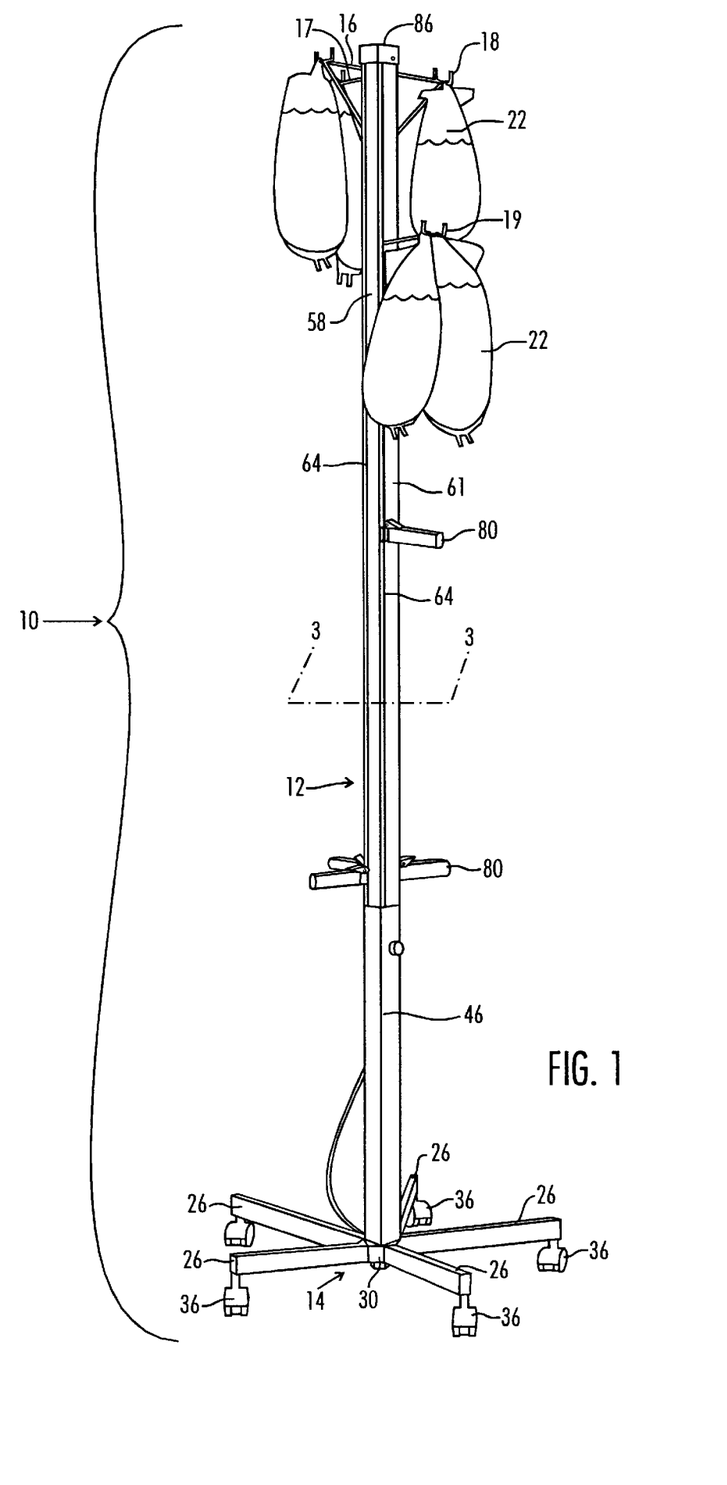
FIG. 1 is a perspective view of an exemplary embodiment of the I.V. pole and irrigation tower of the present invention.

Referring to FIG. 1, a generally rectangular irrigation tower 10 according to an exemplary embodiment of the present invention comprises a trunk pole 12 mounted on a base 14. The trunk pole 12 has four support hangers 16, 17, 18, 19 for supporting fluid bags 22, with each support hanger 16, 17, 18, 19 capable of supporting up to two bags 22.

Figure 2A:
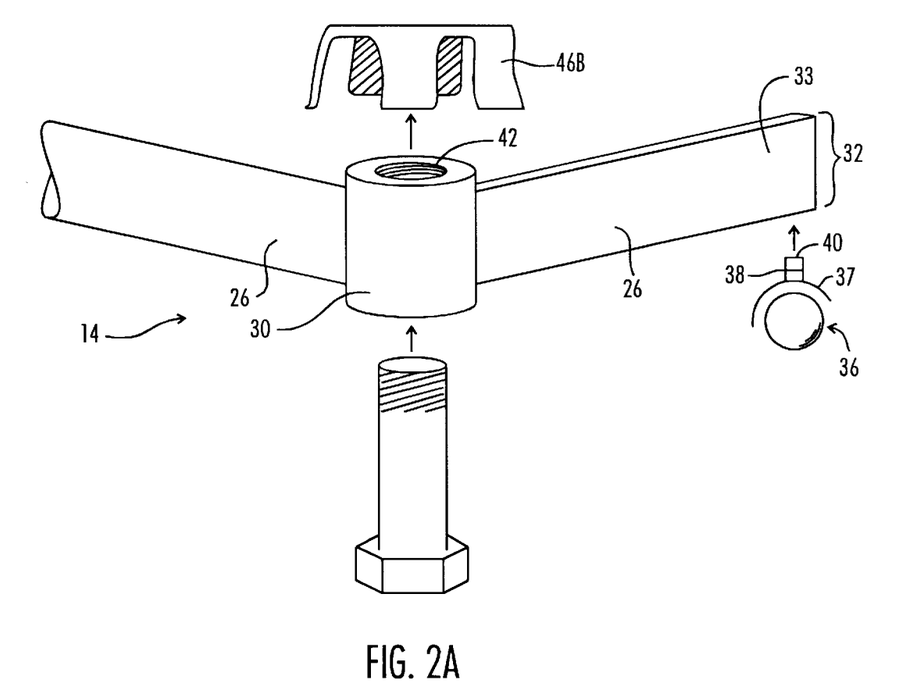
FIG. 2A is an exploded view of a portion of the base of the irrigation tower of FIG. 1.
Figure 2B:
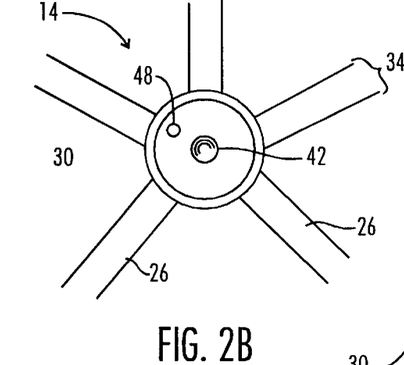
FIG. 2B is a cross-sectional top-plan view of the base of FIG. 2A.
Figure 2C:
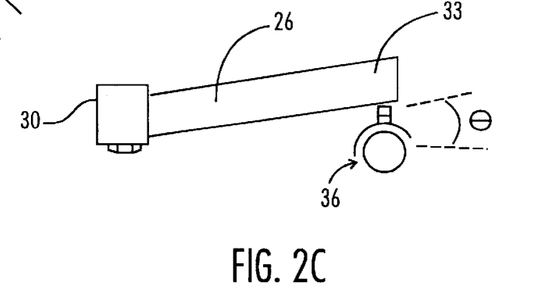
FIG. 2C is a side elevational view of one leg of the base of FIGS. 2A and 2B.
Figure 3:
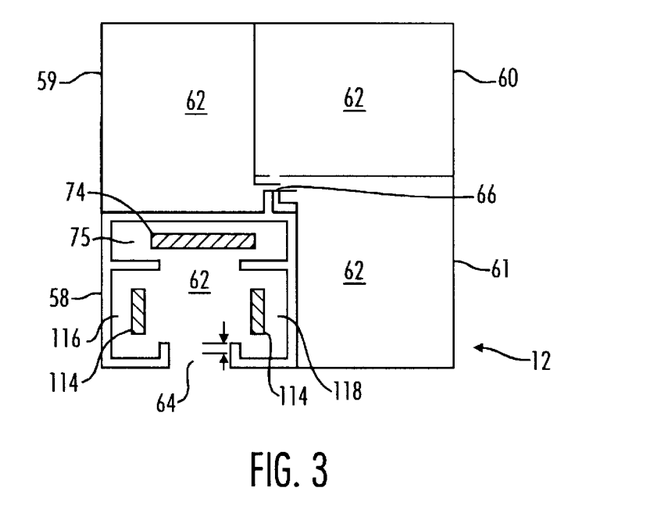
FIG. 3 is a cross-sectional view of the trunk of the irrigation tower of FIG. 1 taken along the lines 3—3 of FIG. 1.
Figure 4:
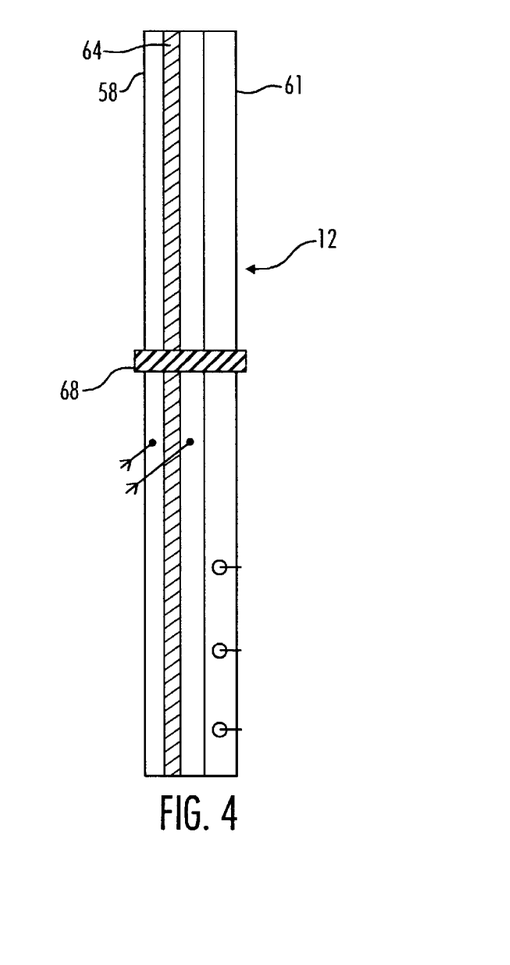
FIG. 4 is a front view of the trunk of the irrigation tower of FIG. 1.

Referring to FIGS. 1–2, the base 14 is comprised of five generally rectangular legs 26, each extending upwardly and outwardly at an angle 0°–10° from a hub 30 of the base 14. Each leg 26 is preferably made from a solid aluminum bar or a steel tube and may be provided with an anodizing or coating of epoxy powder to make the steel tube stain resistant. The vertical width of each leg 32 should be between 1 inch and 4 inches, and preferably about 1½ inches and 2 inches. The thickness 34 of each leg 34 should be between ½ inch and 4 inches, and preferably about ¾ inches. To provide additional stability, it should be appreciated by those skilled in the art that more than five legs may be provided without departing from the spirit and scope of the present invention.

Each leg 26 is equipped with a conventional dual caster 36 to interface the tower 10 with the floor, and to allow the tower 10 to be moved about conveniently. Each dual caster 36 may be a 50 mm or 60 mm plastic dual caster with a retainer ring 38, and is provided with a pin 40 to be fitted in an opening (not shown) at the outer end 33 of the leg 26.

The angled legs 26 function to lower and concentrate the center of gravity of the tower 10 at the hub 30, thereby improving the stability of the tower 10 and minimizing the possibility of the tower 10 toppling over. In operation, the hub 30 should preferably be approximately one inch above the surface of the floor, and the outer end 33 approximately two inches about the surface of the floor.

Figure 9:
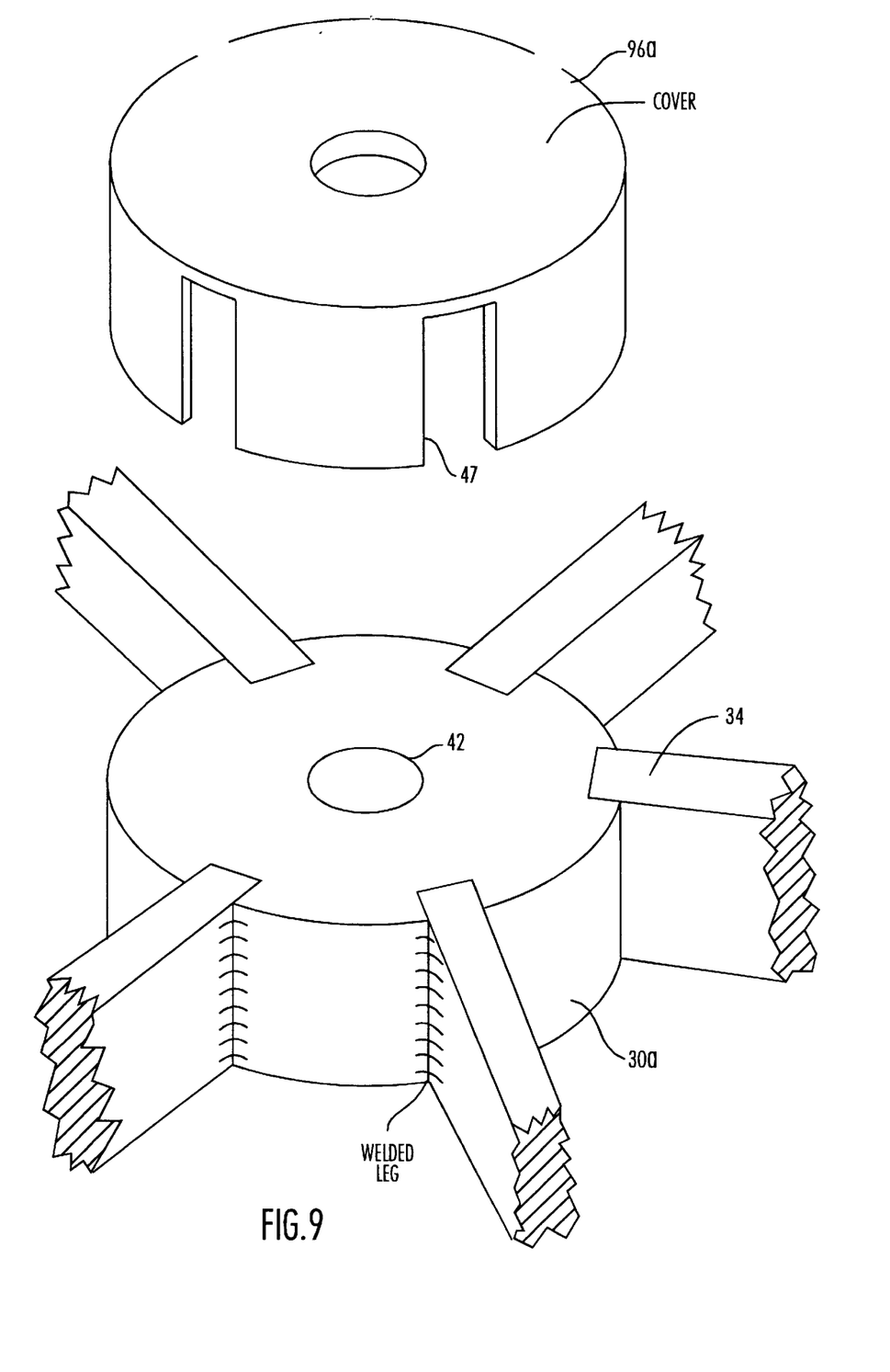
FIG. 9 is another figure showing an alternative cover and hub.

The hub 30 is preferably made from aluminum or steel and has an opening 42 provided therethrough. A bolt 44 is threaded through the opening 42 and through a sleeve 46B and engages internal threads (not shown) provided in a nut plate located at the lower portion of the pole 12 to secure the hub 30 of the base 14 to the pole 12. As illustrated in FIG. 9, an alternative configuration is shown. There, hub 30a has a generally cylindrical configuration with legs 34 dove-tailed and welded thereto. Sleeve or cover 46a is provided with a series of notches 47 into which a portion of legs 34 extend. As previously described, a bolt or other means can be used to secure cover 46a to hub 30a.

The hub 30 is provided with a drainage hole 48. The drainage hole is provided in case liquid has penetrated into the channels from the bags. These liquids are drained to the floor through drainage hole 48.

Referring to FIGS. 1, 3, 4 and 5, the pole 12 comprises four-walled rectangular sections 58, 59, 60, 61. Each section 58, 59, 60, 61 is identical, and each has a channel 62 provided therein and an elongated slot 64 cut out from one of the outward facing walls of the section. The sections 58, 59, 60, 61 are preferably made from anodized aluminum, with each wall having a thickness between 0.050 inches and 0.120 inches, and preferably about 0.0625 inches. The rectangular sections 58, 59, 60, 61 may be extruded as one piece or fastened or secured together by any conventional means to form a unitary square-shaped pole 12. As an example, such fastening means include the provision of interlocking components 66 at the inside walls of the sections 58, 59, 60, 61 at the point where they meet. Alternatively, the support base tube 46 may be used to hold the lower portions of sections 58, 59, 60, 61 together with a band 68 to secure the upper portions. Band 68 also regulates the travel of hangers 16, 17, 18 and 19 such that when the bags 22 are lowered, the operator's hand on handle 80 will not be "pinched" or trapped by the hangers. Or a strong adhesive may be used separately or together with any of the above fastening means. The height of the pole 12 should be between 60 inches and 84 inches, and preferably about 72 inches. The slot 64 extends throughout the length of the pole downwardly from the top of the pole 12, with the support base tube 46 preferably having a length of about 30 inches. It should be appreciated by those skilled in the art that any number of sections can be provided and fastened together without departing from the spirit and scope of the present invention. For example, sections 58, 59, 60 and 61, which comprise pole 12, can be made as one unit. Further, pole 12 could be made generally circular or oval. Further still, while pole 12 is illustrated with four (4) hangers, other configurations, e.g., 1, 2 or 3, are also within the scope of this invention.

Figure 5:
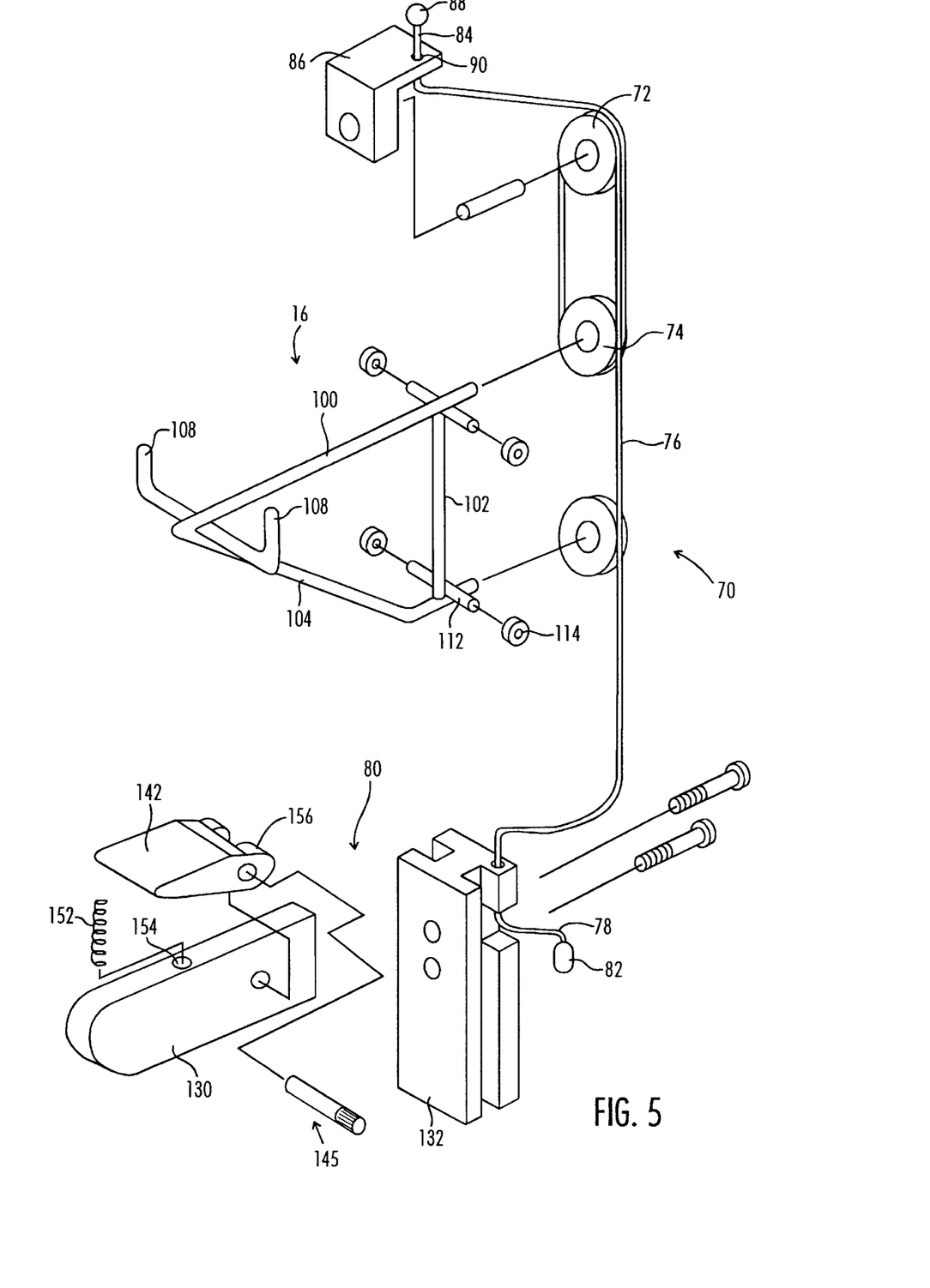
FIG. 5 is an exploded perspective view showing the pulley system of the present invention.

Each channel 62 houses an identical pulley system 70 which is used by the operator to adjust the height of the support hangers 16, 17, 18, 19 from which the fluid bags 22 are supported. Referring to FIGS. 1 and 5, the pulley system 70 has a stationary upper pulley 72 fixed at an upper portion of the channel 62 and a movable lower pulley 74 adapted for vertical movement along an inner track 75. A support hanger 16, 17, 18 or 19 is attached to the lower pulley 74 and extends outwardly through the slot 64. Since each of the pulley systems 70 is identical, only the pulley system for section 58 with respect to the support hanger 16 shall be illustrated and described.

A plastic coated steel cable 76 has a lower end 78 attached to a handle assembly 80 and secured by a metal crimp 82. The upper end 84 of the cable 76 is looped around the upper pulley 72, extended down towards the lower pulley 74, looped around the lower pulley 74 and then extended upwardly through a square-shaped cover 86 and secured to a crimping sleeve 88. The cable 76 should be long enough to extend over and around the pulleys 72 and 74 and allow the lower pulley 74 to be raised to the uppermost point in the slot 64.

Figure 6:
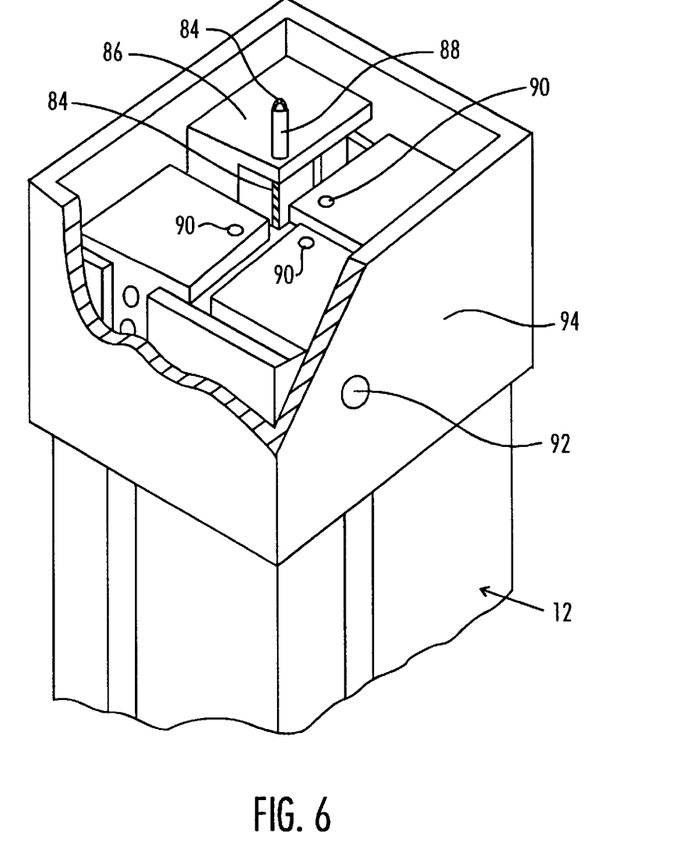
FIG. 6 is a perspective top-plan view of the cover of the irrigation tower of FIG. 1.

Referring to FIG. 6, the pole 12 is fitted with 4 rectangular shaped covers 86, each provided with openings 90, one for each channel 62, through which the steel cable 76 may be passed through and secured by the crimping sleeve 88. Holes 92 are provided on the sleeve sides 94 for passing a screw (not shown) therethrough to secure the 4 covers 86 to the sections 58, 59, 60, 61. The 4 covers 86 and the sleeve 94 are preferably made from metal or hard plastic.

Figure 7A:
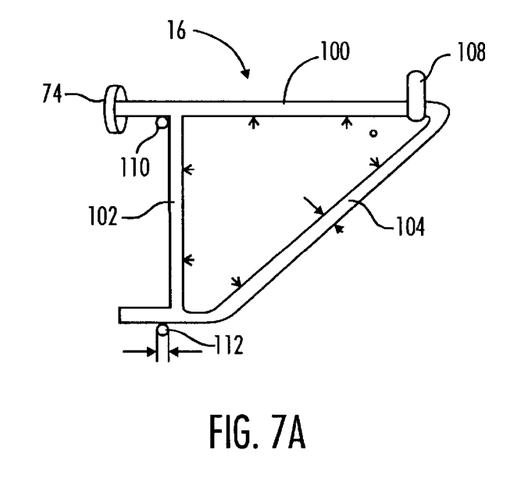
FIG. 7A is a side view of an exemplary embodiment of a support bar used with the irrigation tower of FIG. 1.
Figure 7B:
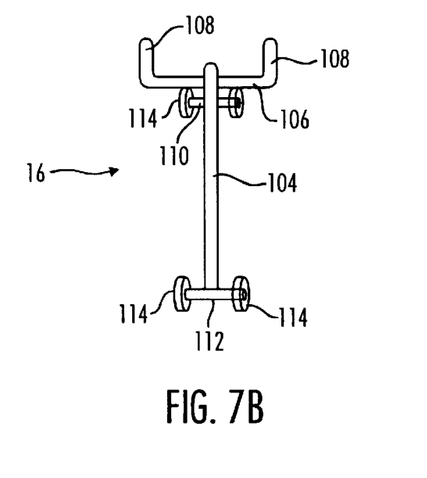
FIG. 7B is a front view of the support bar of FIG. 7A.

The irrigation tower 10 is provided with a total of four support hangers 16, 17, 18, 19. Referring to FIGS. 7A and 7B, each support hanger 16, 17, 18, 19 is made from chrome plated steel or stainless steel and is triangularly-shaped with a horizontal bar 100, a vertical bar 102, and a diagonal bar 104. The horizontal bar 100 has one end attached to the lower pulley 74. A U-shaped bar 106 is secured at a point near the intersection of the horizontal bar 100 and the diagonal bar 104 in an orientation orthogonal to that of the horizontal bar 100 and the diagonal bar 104. The U-shaped hanger 106 has two corners 108 from which a fluid bag 22 may be supported. Thus, each support hanger supports up to two fluid bags 22, so that the irrigation tower 10 allows a maximum of eight fluid bags 22 to be supported therefrom.

Each support hanger 16, 17, 18, 19 is also provided with an upper extension 110 and a lower extension 112. Spacers 114 are provided at both ends of the extensions 110 and 112 for vertical movement along outer tracks 116 and 118 of the channel 62. The spacers 114 are oriented in tracks 116 and 118 in a direction perpendicular to the orientation of the lower pulley 74 in track 75.

The length of the horizontal bar 100 should be between 4 inches and 8 inches, and preferably around 5.75 inches. The length of the U-shaped bar 106 should be between 2 inches and 8 inches, and preferably around 3 inches. The thickness of the stainless steel material used for the support hanger should be between ⅛ inches and ½ inches, and preferably around 0.25 inches.

The pulleys 72 and 74 and spacers 114 are preferably made from nylon or delrin like material. The pulleys 72 and 74 should have a diameter between ½ inches and 1½ inches, and preferably around 0.875 inches.

Thus, the spacers 114 support the entire support bar 16, 17, 18 or 19 for vertical movement in two spaced-apart tracks 116 and 118 while the lower pulley 74 is vertically moved along a separate track 75 in an orthogonal orientation. This coupled with the triangular configuration of the support hangers 16, 17, 18, 19 provide stability to the support of fluid bags 22. It is appreciated by those skilled in the art that many other embodiments of support bars may be used without departing from the spirit and scope of this invention.

Referring to FIGS. 8A–8D, the handle assembly 80 comprises a handle 130 secured to a slider 132. The slider 132 has a rear edge 134 which is fitted in the inner track 75 and front edges 136 which are fitted in the tracks 116 and 118. The slider 132 also has a hole 140 through which the lower end 78 of the cable 76 is attached. The handle 130 extends outwardly from the slot 64 and may be used to slide the slider 132 up and down the corresponding tracks 75, 116 and 118 of the channel 62.

A spring-loaded locking mechanism is provided to lock the handle assembly 80 at a desired location along the slot 64. The locking mechanism comprises an N-shaped release lever 142 having two leg portions 146 and 148 and a bridge section 150. A rotating knurled pin 143 is inserted through an opening 144 in the handle 130 and has its two ends secured to the leg portions 146 and 148 of the lever 142 to secure the lever 142 to the handle 130. A spring 152 extends from a lever spring mount hole 153 in the bridge portion 150 and is attached to a handle spring mount hole 154 in the handle 130. The spring 152 is normally biased to urge the lever 142 upwards, thereby forcing a rear curved portion 156 of the lever 142 against the wall of the section 58. The friction force between the rear curved portion 156 and the section 58 locks the handle assembly 80 in a desired location along the slot 64. To unlock the locking mechanism, an operator presses down on the lever 142 causing the rear curved portion 156 to disengage its contact from the section 58, thereby allowing the handle 130 and slider 132 combination to be freely slid up or down.

Figure 8A:
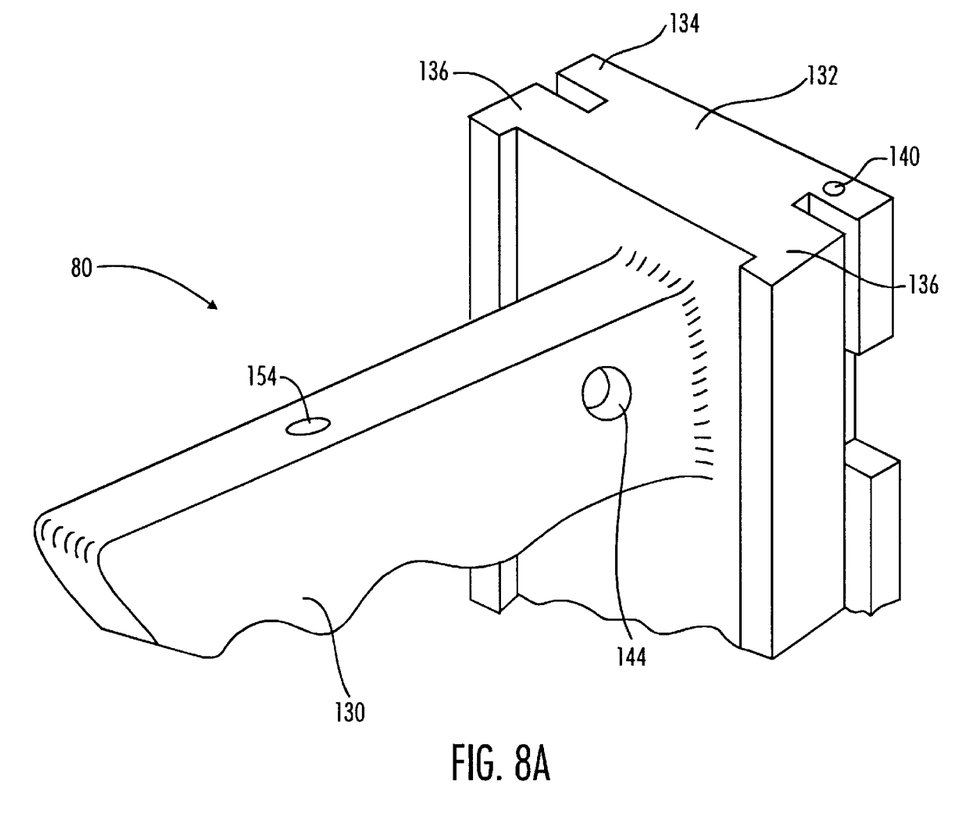
FIG. 8A is a perspective view of the handle assembly of the irrigation tower of FIG. 1.
Figure 8B:
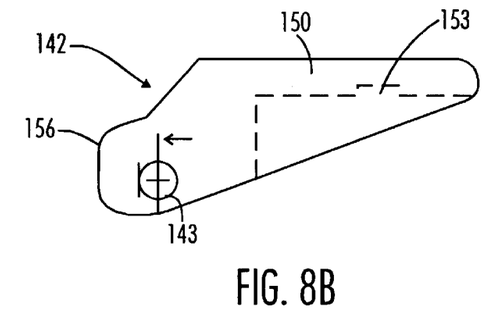
FIG. 8B is a cross-sectional side view of a lever for use with the handle assembly of FIG. 8A.
Figure 8C:
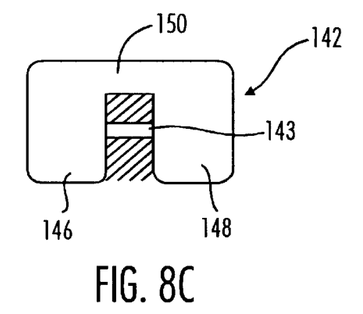
FIG. 8C is a front view of the lever of FIG. 8B.
Figure 8D:
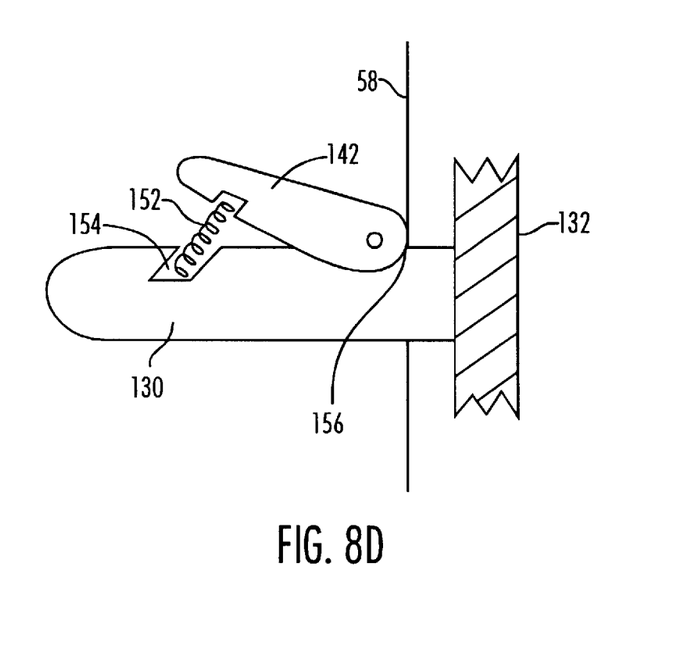
FIG. 8D is a cross-sectional side view of the handle assembly of FIG. 8A illustrating the locking action of the lever of FIGS. 8B and 8C.

The handle 130 is preferably made from aluminum, while the slider 132 and the lever 142 are preferably made from delrin like material, the handle and slider can also be molded from hard plastic as one integrated unit. The handle 130 should be of a length which allows an operator to easily and firmly grip it, and is preferably about 4.5 inches. The length of the slider 132 should between one inch and 6 inches, and preferably about 3 inches. The underside of the handle 130 may be provided with a plurality of curved portions, as shown in FIG. 8A, or may be made horizontal as shown in FIG. 8D, as desired.

Referring to FIG. 5, in operation, when the handle 130 is pulled down, the attached cable 76 is likewise pulled down, thereby shortening the distance between the upper pulley 72 and the lower pulley 74. This causes the lower pulley 74 and its corresponding support hanger 16 to be moved upwardly. Likewise, when the handle 130 is pulled up, the gravitational force of the support hanger and or the fluid bags 22 hanging from the support hanger 16 mounted on the lower pulley 74 pulls the lower pulley 74 and its support hanger 16 downward. The downward movement of the lower pulley 74 causes the distance between the upper pulley 72 and the lower pulley 74 to be increased.

The pulley system 70 is provided to reduce the amount of force that an operator needs to apply in order to move the support bars 16, 17, 18, 19 upwards or downwards. The upper end 84 of the cable 76 is secured to the crimping sleeve 88 of the cover 86 so as to absorb or to concentrate a portion of the force thereon. Thus, an operator may easily adjust the height of the support hangers 16, 17, 18, 19 and the fluid bags 22 thereon without having to exert excessive force or pressure. This allows the height of the support hangers 16, 17, 18, 19 to be easily adjusted between the heights of five to eight feet depending upon the desired fluid pressure.

Further, the locking mechanism of the handle assembly 80 is simple in construction and is easy to use. The configuration of each support hanger 16, 17, 18, 19 provides a stable support for two fluid bags 22. The provision of at least five legs 26 for the base 12 together with their angled orientation provide additional stability to the tower 10 so that a larger number of fluid bags 22 containing a larger volume of fluid can be supported therefrom without any fear of toppling the irrigation tower 10.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An I.V. pole and irrigation tower for use in supporting a plurality of fluid bags, comprising:

a base having a hub and at least four legs spaced apart about the hub, each leg having a first end secured to the hub and a second end extending outwardly at an angle away from the hub, each leg further including a roller secured to the second end;

a pole having a lower end secured to the hub of the base, and a plurality of sections fastened together in interlocking relationship, each section including a channel and a pulley system disposed therein, each pulley system having a support hanger attached thereto for supporting at least one fluid bag, each section further including a handle assembly coupled to the pulley system for adjusting the height of the support hanger along the length of the section;

wherein the channel includes an inner track and two outer tracks positioned orthogonal to the inner track;

wherein the pole further comprises a cover fitted to an upper end of the plurality of sections; and wherein each pulley system comprises an upper pulley secured to a fixed location at an upper end of the inner track, a lower pulley housed in the inner track and having the support hanger attached thereto, a cable having a first end secured to the handle assembly and a second end disposed about the upper pulley and the lower pulley and secured to the cover.

2. The irrigation tower of claim 1, wherein each section is comprised of four walls defining the channel, one of the walls having an elongated slot through which the support hanger extends outwardly from its attachment to the lower pulley.

3. The irrigation tower of claim 2, wherein the handle assembly comprises a slider housed in the channel for vertical movement therein, the first end of the cable secured to the slider, the handle assembly further comprising a handle attached to the slider and extending outwardly through the slot.

4. The irrigation tower of claim 3, wherein the handle assembly further comprises a spring-biased lever coupled to the handle for locking the handle assembly and support hanger at a desired location along the length of the section.

5. The irrigation tower of claim 4, further comprising a spring having a first end attached to the lever and a second end attached to the handle, wherein the spring is normally biased to cause the lever to engage the section to prevent the handle assembly from being moved vertically.

6. The irrigation tower of claim 4, wherein the handle has a substantially horizontal top surface, the lever is pivotally connected to the handle and extends along the top surface, the lever has a locking surface which faces the associated pole section, and the lever is spring-biased in a direction to press the locking surface against the pole section in order to fix the handle assembly in position relative to the pole.

7. An I.V. pole and irrigation tower for use in supporting a plurality of fluid bags, comprising:

a base having a hub and at least four legs spaced apart about the hub, each leg having a first end secured to the hub and a second end extending outwardly at an angle away from the hub, each leg further including a roller secured to the second end;

a pole having a lower end secured to the hub of the base, and a plurality of sections fastened together in interlocking relationship, each section including a channel and a pulley system disposed therein, each pulley system having a support hanger attached thereto for supporting at least one fluid bag, each section further including a handle assembly coupled to the pulley system for adjusting the height of the support hanger along the length of the section;

wherein each section is comprised of four walls defining the channel, one of the walls having an elongated slot through which the support hanger extends outwardly from its attachment to the pulley system, the handle assembly comprises a slider housed in the channel for vertical movement therein, the first end of the cable secured to the slider, the handle assembly further comprising a handle attached to the slider and extending outwardly through the slot, and the handle assembly further comprises a spring-biased lever coupled to the handle for locking the handle assembly and support hanger at a predetermined location along the length of the section.

8. An I.V. pole and irrigation tower for use in supporting a plurality of fluid bags, comprising:

a base having a hub and at least four legs spaced apart about the hub, each leg having a first end secured to the hub and a second end extending outwardly at an angle away from the hub, each leg further including a roller secured to the second end;

a pole having a lower end secured to the hub of the base, and a plurality of sections fastened together in interlocking relationship, each section including a channel and a pulley system disposed therein, each pulley system having a support hanger attached thereto for supporting at least one fluid bag, each section further including a handle assembly coupled to the pulley system for adjusting the height of the support hanger along the length of the section;

wherein each pulley system comprises:
  an upper pulley secured to a fixed location at an upper end of the channel;
  a lower pulley housed in the channel and having the support hanger attached thereto; and
  a cable having a first end secured to the handle assembly and a second end fixed to the pole at the upper end of the channel, said cable extending about the upper pulley and the lower pulley.

9. The irrigation tower of claim 8, wherein each section is comprised of four walls defining the channel, one of the walls having an elongated slot through which the support hanger extends outwardly from its attachment to the lower pulley.

10. The irrigation tower of claim 9, wherein the handle assembly comprises a slider housed in the channel for vertical movement therein, the first end of the cable secured to the slider, the handle assembly further comprising a handle attached to the slider and extending outwardly through the slot.

11. An ambulatory supporting apparatus for movably supporting heavy loads comprising:

(a) a central standard comprising a plurality of vertically disposed, parallel tracks;

(b) a base including a hub coupled to said central standard, at least five supporting legs extending outwardly and upwardly from said hub and being uniformly spaced about said hub, and ambulatory means coupled to each of said supporting legs for movement over a horizontal surface;

(c) hanger means for supporting the loads, said hanger means being slidably coupled within each of said parallel tracks;

(d) a positioning arm slidably coupled within each of said parallel tracks; and (e) force transfer means coupled intermediate each of said load supporting hanger means and a respective positioning arm for moving said hanger means within said track in an inverse response to the movement of said positioning arm.

12. An ambulatory supporting apparatus as defined in claim 11 wherein said tracks each comprise a rear wall, a pair of side walls integral with and perpendicular to each end of said rear wall and first and second-aligned frontal flanges parallel to said rear wall and depending inwardly from aid side walls and first and second aligned interior flanges depending inwardly from said slide walls between said frontal flanges and said rear wall, said first and second frontal flanges proscribing a longitudinal aperture therebetween in communication with a first cavity bounded by said rear wall, side walls and said first and second interior flanges and said first and second aligned frontal flanges.

13. An ambulatory supporting apparatus as defined in claim 12 wherein said hanger means comprises a horizontal supporting rod extending through the aperture proscribed by said first and second aligned frontal flanges and into said first cavity, and roller means coupled to said horizontal supporting rod for supporting said rod slidingly disposed within said second cavity bounded by said first and second frontal flanges and said first and second interior flanges.

14. An ambulatory supporting apparatus as defined in claim 13 wherein said force transfer means comprises:
 (a) a first pulley rotatably journeled about said horizontal supporting rod within the first cavity of said track bounded by said rear wall and said first and second interior flanges;
 (b) a second pulley rotatably coupled about an axle extending between the rear wall and first and second interior flanges and disposed within the first cavity bounded by the rear wall and said first and second interior flanges; and
 (c) positional means coupled to said first and second pulleys and to said positioner arm for transferring rod in an inverse relationship to the direction of movement of said positioner arm.

15. An ambulatory supporting apparatus comprising:
 (a) a base consisting of a hub and at least five equally separated supporting legs extending outwardly and upwardly from said hug, the end of each of said supporting leg opposite said hug being coupled to a rotatable roller;
 (b) a plurality of extruded tracks placed adjacent one another and having first and second ends, the second ends of said extruded tracks being coupled to said hug and extending upwardly therefrom, each of said tracks comprising a rear wall, a pari of slide walls integral with and perpendicular to said rear wall, first and second aligned frontal flanges parallel to said rear wall and depending inwardly from side walls and defining a longitudinal aperture therebetween extending from the first end to the second end of said track in communication with a first cavity bounded by said rear wall, side walls and first and second interior flanges and a second cavity bounded by said first and second interior flanges and said first and second aligned frontal flanges, the longitudinal apertures of said adjacent tracks being separated by 90° of arc;
 (c) a load supporting hanger, and end thereof being in communication with the first and second cavities of each of said tracks, each said load supporting hanger including a horizontal supporting rod extending between said first and second frontal flanges of aid respective track and into the first cavity and roller means coupled to aid horizontal supporting rod for supporting said adjacent said supporting rod and being rollingly disposed within said second cavity;
 (d) a positioning arm slidably coupled within each of said extruded tracks and extending between said first and second frontal flanges;
 (e) an engagement lever coupled to said positioning arm and adapted to resiliently exert frictional force against first and second frontal flanges; and
 (f) force transfer means coupled intermediate said load supporting hanger and a respective one of said positioning arms for moving said load supporting hanger within said extruded track and inverse response to the movement of said positioning arm.

16. An ambulatory supporting apparatus as defined in claim 15 wherein force transfer means comprises:
 (a) a first pulley rotatably journeled about said horizontal supporting rod within the first cavity of aid extruded track;
 (b) a second pulley rotatably coupled about an axle extending between and being perpendicular to the rear wall and first and second frontal flanges of each of said extruded tracks and being rotatably disposed within the first cavity; and
 (c) positional means coupled to said first and second pulley and to said positioner arm for transferring directional movement to said horizontal supporting rod in an inverse relationship to the direction of movement of said positioner arm.

\* \* \* \* \*